(12) United States Patent
Laugere et al.

(10) Patent No.: US 9,889,260 B2
(45) Date of Patent: Feb. 13, 2018

(54) DISPENSE INTERFACE

(71) Applicant: SANOFI-AVENTIS DEUTSCHLAND GMBH, Frankfurt am Main (DE)

(72) Inventors: Frederic Laugere, Bedfordshire (GB); Cristian Popa, Norfolk (GB); Ben Impey, Cambridgeshire (GB); Andrew MacLeod, Cambridgeshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 115 days.

(21) Appl. No.: 14/395,993

(22) PCT Filed: May 16, 2013

(86) PCT No.: PCT/EP2013/060164
§ 371 (c)(1),
(2) Date: Oct. 21, 2014

(87) PCT Pub. No.: WO2013/171311
PCT Pub. Date: Nov. 21, 2013

(65) Prior Publication Data
US 2015/0320942 A1 Nov. 12, 2015

(30) Foreign Application Priority Data
May 16, 2012 (EP) .................................. 12168374

(51) Int. Cl.
*A61M 5/32* (2006.01)
*A61M 5/14* (2006.01)
(Continued)

(52) U.S. Cl.
CPC ........ *A61M 5/3294* (2013.01); *A61M 5/1407* (2013.01); *A61M 5/16827* (2013.01);
(Continued)

(58) Field of Classification Search
CPC ................ A61M 5/3294; A61M 5/329; A61M 5/16827; A61M 5/1407; A61M 5/31596;
(Continued)

(56) References Cited

U.S. PATENT DOCUMENTS 533,575 A 2/1895 Wilkens
4,610,666 A 9/1986 Pizzino
(Continued)

FOREIGN PATENT DOCUMENTS

CN 1064622 A 9/1992
CN 101400390 A 4/2009
(Continued)

OTHER PUBLICATIONS

International Search Report for Int. App. No. PCT/EP2013/060164, completed Aug. 9, 2013.
(Continued)

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

The invention relates to a dispense interface comprising a body comprising at least a first channel structure and a second channel structure, wherein each of the at least two channel structures comprises at least a first inlet channel comprising a first inlet opening and a second inlet channel comprising a second inlet opening, wherein each of the at least two inlet openings of one channel structure is configured for fluid communication with a respective reservoir of at least two reservoirs and wherein at least one connecting channel configured for a fluid communication between at least one outlet opening and one of the at least two channel structures is provided.

14 Claims, 15 Drawing Sheets

(51) Int. Cl.
   *A61M 5/168* (2006.01)
   *A61M 5/19* (2006.01)
   *A61M 5/315* (2006.01)
   *A61M 39/22* (2006.01)
   *A61M 5/31* (2006.01)

(52) U.S. Cl.
   CPC .......... *A61M 5/19* (2013.01); *A61M 5/31596* (2013.01); *A61M 5/329* (2013.01); *A61M 39/223* (2013.01); *A61M 2005/3128* (2013.01)

(58) Field of Classification Search
   CPC ................ A61M 5/19; A61M 15/0045; A61M 15/0048; A61M 2005/004; A61M 2005/005
   See application file for complete search history.

(56) References Cited

U.S. PATENT DOCUMENTS

| | | | |
|---|---|---|---|
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,417,667 A | 5/1995 | Tennican et al. | |
| 5,478,323 A * | 12/1995 | Westwood | A61M 5/19 604/191 |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,916,201 A | 6/1999 | Wilson et al. | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,416,540 B2 * | 8/2008 | Edwards | A61M 5/19 604/144 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2008/0147014 A1 | 6/2008 | Lafferty | |
| 2009/0275916 A1 | 11/2009 | Harms et al. | |

FOREIGN PATENT DOCUMENTS

| | | |
|---|---|---|
| CN | 101945678 A | 1/2011 |
| EP | 0937471 | 8/1999 |
| EP | 0937476 | 8/1999 |
| EP | 2283885 | 2/2011 |
| WO | 94/22507 | 10/1994 |
| WO | 99/38554 | 8/1999 |
| WO | 01/10484 | 2/2001 |

OTHER PUBLICATIONS

Chinese Office Action for CN Application No. 201380023499.1, dated Jun. 3, 2016.

* cited by examiner

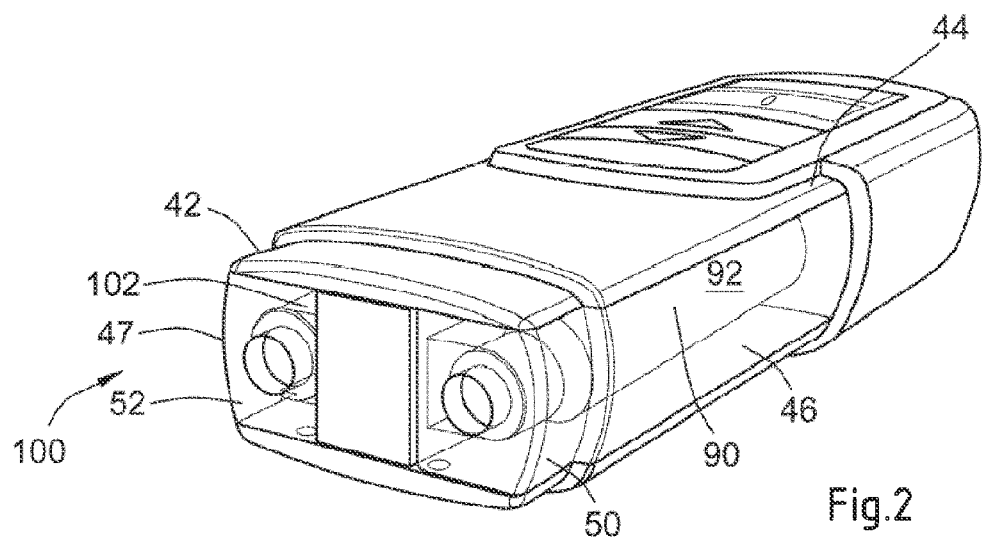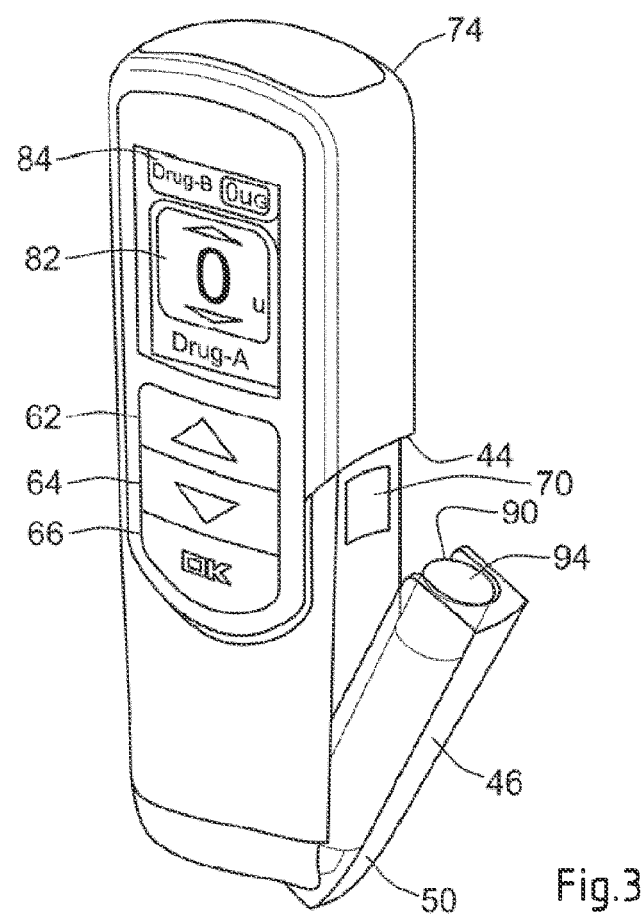

DISPENSE INTERFACE

CROSS REFERENCE TO RELATED APPLICATIONS

The present application is a U.S. National Phase Application pursuant to 35 U.S.C. §371 of International Application No. PCT/EP2013/060164 filed May 16, 2013, which claims priority to European Patent Application No. 12168374.2 filed May 16, 2012. The entire disclosure contents of these applications are herewith incorporated by reference into the present application.

TECHNICAL FIELD

The present patent application relates to an ejection device, for example a medical device, for delivering at least two liquids, such as liquid drug agents, from separate reservoirs. Such drug agents may comprise a first and a second medicament. The medical device includes a dose setting mechanism for delivering the drug agents automatically or manually by the user.

SUMMARY

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The dispense interfaces in the state of the art are, however, often of complex design. In order to provide the manifold to lead the medicaments from two different reservoirs to a single outlet, multiple complex and/or small parts need to be produced and assembled. A dispense interface in the state of the art normally has one channel structure with at least two inlet channels.

The dispense interface is regularly kept at the drug delivery device for a longer period of time. This means that only the dose dispenser in form of a double ended needle, for instance, is exchanged for every or nearly every injection procedure. The dispense interface, however, remains at the drug delivery device. The same channel structure is used a plurality of times. An exchange of the dispense interface itself is regularly only necessary, when the reservoirs of the drug delivery device need to be exchanged.

This causes requirements for the material and design of the dispense interface to be fulfilled. Since the drug agents from the first and/or the second reservoir remain inside the dispense interface, e.g. in the inlet channels of the channel structure, after a dispense procedure, a material compatibility of these parts of the dispense interface being in contact with the drug agents needs be to provided. No harmful substances must diffuse into the drug agents, since these would then be delivered to the patient with the next delivery procedure. Hence a biocompatibility is required, which guarantees that either no or negligible amounts of substances can diffuse into drug agents or are set free into the liquid.

Another option for guaranteeing that either no or only negligible amounts of substances can diffuse into drug agents or are set free into the liquid is the use of single use dispense interfaces. In particular, a dispense interface is used for only one ejection or injection procedure. In this case, the drug is in contact with parts of the dispense interface, like the inlet channel, for a short time period. Due to the short time period, either no or negligible amounts of substances can diffuse into the drug agents. However, an obvious disadvantage of single use dispense interfaces is that after every ejection procedure the used dispense interface has to be disposed. In particular, for environmental reasons single use dispense interfaces should be avoided.

In light of the aforementioned, the invention faces the technical problem of material compatibility and cross contamination and at the same time, overcoming the environmental problems.

The technical problem is solved by a dispense interface comprising a body comprising at least a first channel structure and a second channel structure, wherein each of the at least two channel structures comprises at least a first inlet channel comprising a first inlet opening and a second inlet channel comprising a second inlet opening, wherein each of the at least two inlet openings of one channel structure is configured for fluid communication with a respective reservoir of at least two reservoirs and wherein at least one connecting channel configured for a fluid communication between at least one outlet opening and one of the at least two channel structures is provided.

By providing a body comprising at least two channel structures, wherein each channel structure is preferably configured for (only) one ejection procedure, the dispense interface can be used at least for two ejections. More particularly, a multi-use dispense interface with a plurality of single-use channel structures can be provided. The discarding of the dispense interface after every ejection can be avoided, which is advantageous in view of environmental reasons.

The dispense interface is particular suitable for an ejection device. Furthermore, the production of the dispense interface is also more cost-efficient than the production of single use dispense interfaces since it is not required to produce a plurality of single-use dispense interfaces. Merely one multi-use dispense interface with a plurality of single-use channel structures can be produced. As a consequence, the total productions costs and efforts are reduced.

During an ejection procedure a liquid may enter the dispense interface through the first inlet opening of a first channel structure and another liquid may enter the dispense interface through the second inlet opening of the first channel structure. Guided by the respective inlet channels of the first channel structure and the connecting channel, the liquids can leave the dispense interface via the outlet opening. The dispense interface can thus be seen as a manifold.

Since a channel structure of the dispense interface is only in connection with the reservoirs of the ejection device substantially during the ejection procedure, there is only a short time for possible substances or chemicals in the dispense interface to diffuse into the liquid ejected by the ejection device and guided through the inlet, connecting and/or outlet channels.

There is also substantially no time for the liquids within the reservoirs to become cross-contaminated, since each channel structure is preferably used for only one ejection. After all channel structures has been used for a respective number of ejection procedures, the dispense interface can be discarded.

It shall be understood that, generally, every channel structure can also be used for two or more ejections.

As a consequence of the above mentioned, an easy usage of a multi-use dispense interface is provided and at the same time the problems of material compatibility and cross contamination as well as environmental problems are overcome.

According to an embodiment of the dispense interface according to the invention, at least one separate member comprising at least the at least one connecting channel and the at least one outlet opening is provided, wherein the separate member is configured for a fluid tight connection with the body. For instance, suitable connecting elements are provided for establishing a fluid tight connection between the body and the separate member. Thereby, the connecting channel can be configured for a fluid connection between an outlet of the first inlet channel and an outlet of the second inlet channel of one channel structure. Thereby, the separate member, in particular, the connecting channel, may be configured to establish a respective fluid communication with all channel structures of the body.

Furthermore, the outlet opening of the separate member may be provided with a further connecting element configured for a connection with a second needle assembly. The second needle assembly attached to the separate member, corresponding to the outlet opening, can serve as a dose dispenser comprising an injection needle, for example. Preferably, the separate member can be a single-use item. After the ejection procedure, the separate member can be disconnected from the multi-use body. Preferably, the separate member is used for only one ejection procedure.

In another embodiment of the dispense interface according to the invention, a first double-ended needle assembly comprising at least a first double-ended needle and a second double-ended needle is provided, wherein the first double ended needle assembly is configured for a fluid tight connection with the at least two inlet openings of one channel structure. For instance, the double ended needle assembly is a separate component. The body may have at least one connecting element corresponding to at least one connecting element of the first double-ended needle assembly for securely connecting the respective components to each other. The first double-ended needle assembly may comprise a first piercing needle and a second piercing needle. The first and second needle may correspond to the first and second inlet opening of one channel structure, respectively. The needles can be inserted into the respective openings.

In particular, double ended needles are provided. The needles may be configured to pierce for example the septa of the corresponding reservoirs. The needles of the first double ended needle assembly may guide the liquids of the reservoirs to the first and second opening of one channel structure of the dispense interface.

The first double ended needle assembly may be a single use item. After the ejection process, the first double-ended needle assembly can be disconnected from the body. Preferably, the first double-ended needle assembly is used for only one ejection procedure.

Furthermore, according to another embodiment of the dispense interface of the invention, the body is formed as a cylinder comprising a distal end surface and a proximal end surface, wherein at least two inlet openings of at least one channel structure are arranged at an edge region of the proximal end surface. In particular, the body may be a drum. Preferably, all inlet openings of the respective channel structures are arranged at the edge region of the proximal end surface. The end surfaces may have a circular shape. The distances between the respective two inlet openings of each channel structure may be substantially equal. The distance between the two openings of one channel structure, preferably of each channel structure, may correspond to the distance of the first and second reservoir of the ejection device. All channel structures can be easily connected with the respective reservoirs, for instance, by a first double ended needle assembly.

In particular, according to a further embodiment, the at least two inlet openings of at least one channel structure are arranged on a straight line which passes the center of the proximal end surface. By the arrangement of the inlet openings on a straight line which passes the center of the proximal end surface at the edge region of a circular surface, the provided surface can be used efficiently. In particular, all openings may be arranged on a circular path of the drum.

According to another preferred embodiment of the dispense interface of the invention, the body comprises at least a first part and a second part, wherein the first part provides a cylindrical axis on which a second cylindrical part can be mounted, the first part comprising the at least one outlet opening and the at least one connecting channel and wherein the second part comprises at least the first channel structure and the second channel structure. By providing a second part comprising two or more channel structures rotatably mounted on the first part, a user can easily switch from a first channel structure to a second channel structure, for instance after an ejection procedure. By providing a first part in the form of a longitudinal axis and a second part rotatably mounted on this axis, the user can switch between at least two channel structures by simply rotating the second part. An easy and user-friendly handling of the dispense interface can be provided.

Preferably, all inlet openings of the respective channel structures are arranged at the edge region the proximal end surface of the second part. The distance between the two openings of one channel structure, preferably of each channel structure, may correspond to the distance of the first reservoir and second reservoir of the ejection device. All channel structures can be easily connected with the respective reservoirs, for instance, by a first double ended needle assembly.

It is further preferred that the first part comprises a first double-ended needle assembly, wherein the first double-ended needle assembly is arranged at the proximal end of the first part in such a way that the first double-ended needle assembly is tightly connectable with the at least two inlet openings of one channel structure of the second part. The first double ended needle assembly may be formed as an integral component of the first part. The double ended needle assembly may be designed in such a way that it can be used for a plurality of ejections. In particular, the double ended needle can be configured to be used at least as often as corresponds to the number of channel structures in the second part. A suitable material can be used with a required biocompatibility. The first double ended needle assembly can be configured for a fluid connection between a first reservoir and a first inlet opening of a channel structure and for a fluid connection between a second reservoir and a second inlet opening of the channel structure.

According to a further embodiment, a stop element is arranged at the distal end of the first part, wherein at least one elastic element is arranged between the stop element and the second part and wherein the elastic element is configured to exert a force onto the second part into the proximal direction. By providing an elastic element which exerts a force in the proximal direction, in particular along the axis of the first part, it can be ensured that a fluid tight connection is formed between the first double-ended needle assembly and the openings of at least one channel structure. The elastic element is preferably a spring, in particular, a helical spring. A helical spring can be easily mounted on the first part between the second part and the stop element.

According to another embodiment, the second part is configured to release the fluid tight connection between the first double-ended needle assembly and the at least two inlet openings of a first channel structure by a movement in a distal direction. The second part is further configured to establish a fluid tight connection between the first double-ended needle assembly and the at least two inlet openings of a second channel structure by a rotational movement and a movement in a proximal direction of the second part. The user can switch from a first channel structure to a second channel structure in a simple way. For instance, in a first step, the user can push the second part into the distal direction of the dispense interface along the axis of the first part. Thereby, the force to be exerted by the user must be larger than the force exerted by the at least one elastic element. If the needles of the first double-ended needle assembly are exposed, the second part can be freely rotated. In particular, the user can rotate the second part until the first and second inlet opening of an e.g. unused channel structure is located opposite the respective needles of the first double ended needle assembly. If the user releases the second part, the force exerted by the elastic element causes that the respective needles to enter the respective inlet openings and a fluid tight connection is established. An easy and user-friendly handling of the dispense interface can be provided.

Furthermore, it is preferred that at least one inlet opening is sealed by a pierceable material. For instance, a rubber seal or a film can be provided. The material of the film or layer may be metal, polymer and/or biopolymer. Preferably, a layer is bonded to the distal end surface comprising the at least one inlet opening. For instance, adhesive bonding techniques and/or thermal bonding techniques, such as fusion or laser techniques, can be used. In particular, all inlet openings are sealed by a pierceable material. A sealing layer can prevent particles from entering into a channel structure, in particular an unused channel structure. Furthermore, a user can recognize which channel structures have already been used and which are still unused.

According to a further embodiment, at least one part of the body is produced by injection molding. With this manufacturing process at least one of the parts can be produced from plastic, such as a thermoplastic or a thermosetting material. It is preferred that both or all parts are produced from plastic. This reduces the operating expenses and costs of the manufacturing process of the dispense interface making it suitable for a low cost multi use component.

When the inlet and connecting channels are configured such that a liquid can flow freely from any region of higher pressure to any region of lower pressure, the dispense interface is particularly easy and cost efficient to manufacture. No components, in particular valves, are provided in the inlet and connecting channels, which would increase the efforts and expenses during the manufacture of the dispense interface. The risk of a cross-contamination or a diffusion of substances into the liquid guided with the dispense interface is counteracted by the fact that one channel structure of the dispense interface can be only used for one ejection procedure. Hence, there is only a short period of time, in which the guided liquid and the respective channel structure of the dispense interface are in contact reducing the risk of any contaminations of the dispense interface.

Alternatively, it is also possible, that at least one non return valve is provided. In particular, the connecting channel may comprise such a valve. This prevents or minimizes the back flow of a fluid back into one of the reservoirs. Additionally, the common volume can be reduced, in which both fluids from the reservoirs mix. This is advantageous, in case the user forgets to remove the dispense interface from the ejection device. In that case a cross-contamination can still be prevented. Especially, when the fluids are ejected one after another, the risk of a cross-contamination is higher, since there is a reduced counter pressure for the fluid from the one reservoir to enter the other reservoir compared to when both fluids are ejected simultaneously. Preferably, either a valve, such as a diaphragm valve, for each the first and the second inlet channels is provided or a valve, such as a shuttle valve, which prevents backflow in both the first and the second inlet channels is provided. In case more than two inlet channels are provided, a corresponding number of valves is preferably provided.

The at least one valve can either be an integral part of the dispense interface. Alternatively the at least one valve can also be designed as a separate part and then assembled with the body and/or the separate member. Possible valves are for example a diaphragm or flap valve, a shuttle valve, a molded duck bill valve, a flat spring, or rotation flap valve.

The technical problem is further solved by a system comprising a dispense interface according to the invention and an ejection device, wherein the dispense interface is attachable to the ejection device. For instance, the user can attach the dispense interface by a first double ended needle assembly to the ejection device. For this, connection elements of the respective components are adapted to each other. In particular, a fluid connection between two inlet channels of a preferably unused channel structure and at least one reservoir of the ejection device can be established. For instance, the user can rotate a body in the form of a drum until two unused inlet openings match the respective needles of the first double ended needle assembly.

As a consequence, the dispense interface can be used for a plurality of ejections, wherein the number of ejections may correspond to the number of channel structures. After all channel structures have been used, the dispense interface can be discarded.

The technical problem is further solved by a method for using a previously described dispense interface comprising the steps of attaching a first double ended needle assembly to the inlet openings of one channel structure of the dispense interface and attaching the dispense interface to an ejection device having at least two reservoirs such that a fluid tight connection is established between the at least two reservoirs and the channel structure of the dispense interface.

If a first double ended needle assembly is not an integral part of the body, a respective double ended needle assembly can be attached to each of the inlet openings of an unused channel structure of the dispense interface. If the double ended needle assembly is part of a first part of the body, the respective double ended needle assembly can be attached to the inlet openings of an unused channel structure of the second part of the body of the dispense interface.

When the user attaches the dispense interface to the ejection device, preferably the first needle of the double ended needle assembly provides a fluid tight connection to the first reservoir of the ejection device, for example by piercing a septum of the first reservoir, while the second needle of the double ended needle assembly provides a fluid tight connection to the second reservoir of the ejection device, for example by piercing a septum of the second reservoir.

The dispense interface may be secured in an engaged position with the ejection device. This can be done by fixing elements provided by the ejection device, for example. Such fixing elements, hooks or protrusions adapted to the dispense interface for instance, may establish a positive fit between the dispense interface and the ejection device. Alternatively, it is also possible that the dispense interface is fixed in the engaged position with the ejection device only by friction fit.

In case the needle tips of the first double ended needle assembly are covered with needle covers, the user needs to remove these covers before attaching the dispense interface to the ejection device. In case the needle tip of the second needle assembly is covered with a needle cover, the user needs to remove this cover before performing an ejection procedure.

Preferably, the method according to the invention further comprises the steps of ejecting a fluid from at least one of the reservoirs through the dispense interface and then removing the dispense interface form the ejection device.

These steps are performed after having attached the dispense interface to the ejection device. When another ejection should be performed, a user can choose an unused channel structure of the body, for instance, by rotating the body. After all channel structures have been used, the dispense interface can be discarded. When a used channel structure of the dispense interface is removed after an ejection procedure, for example by the user, the risk of possible contaminations of the fluids and/or the reservoirs is reduced.

These as well as other advantages of various aspects of the present invention will become apparent to those of ordinary skill in the art by reading the following detailed description, with appropriate reference to the accompanying drawings, in which:

BRIEF DESCRIPTION OF THE FIGURES

FIG. 2 illustrates a perspective view of the delivery device distal end showing the cartridge;

FIG. 3 illustrates a perspective view of the delivery device illustrated in FIG. 1 or 2 with one cartridge retainer in an open position;

DETAILED DESCRIPTION

Figure 1:
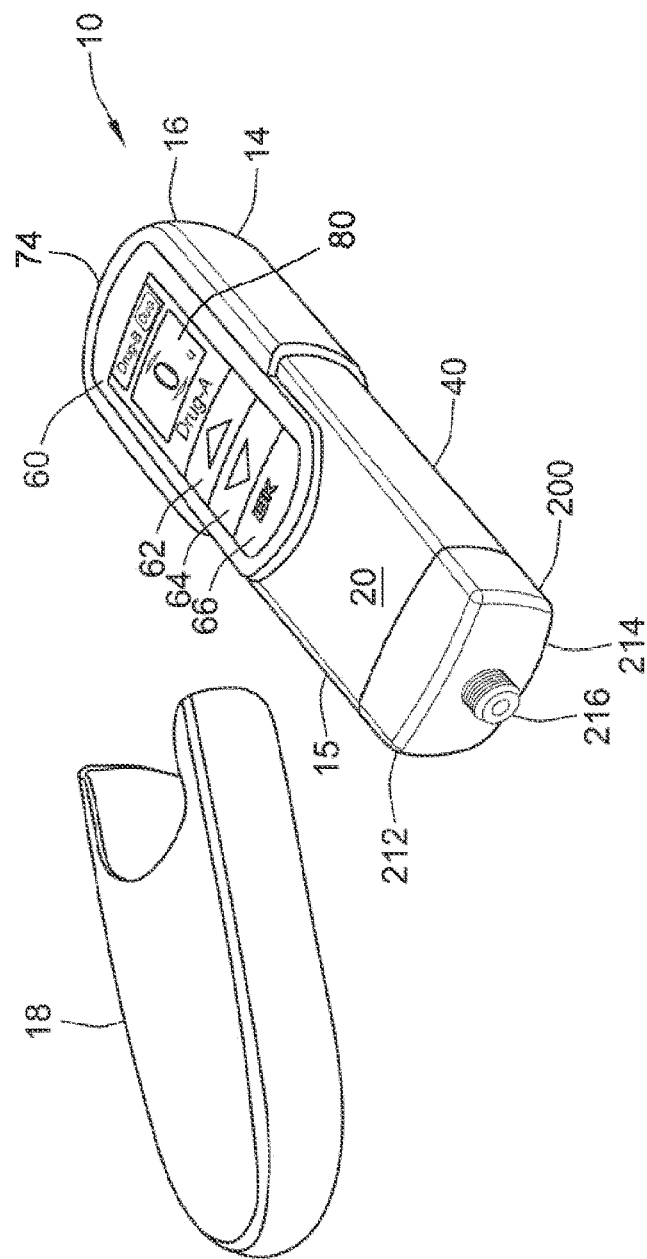
FIG. 1 illustrates a perspective view of a delivery device with an end cap of the device removed.

The ejection device in the form of a drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) can be attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
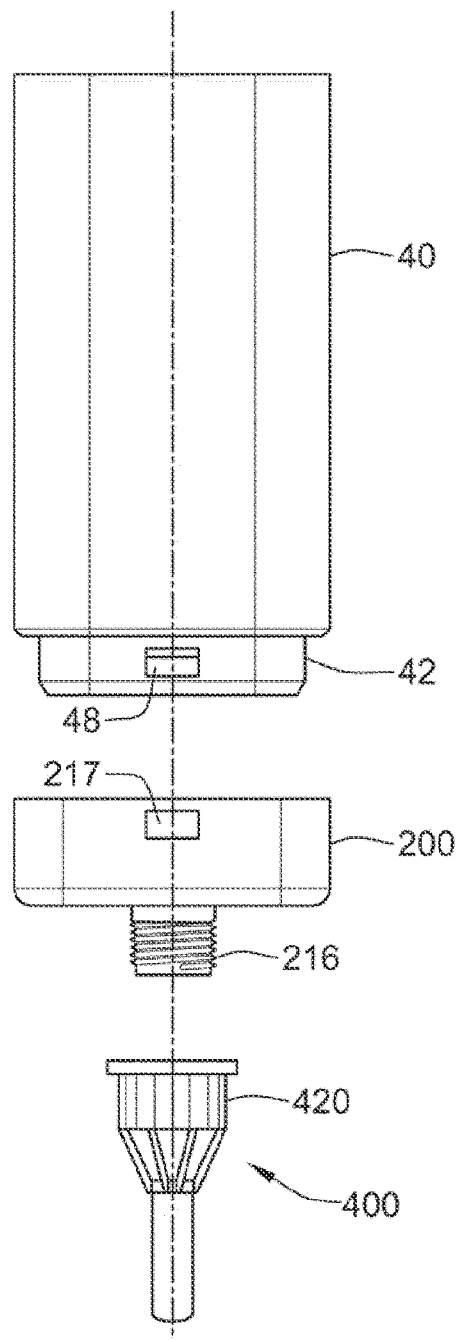
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
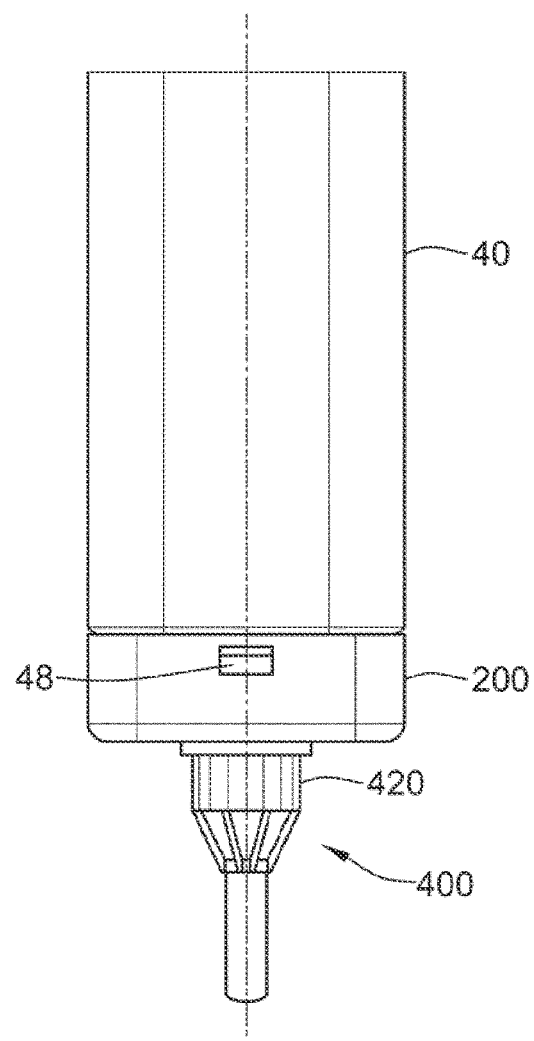
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
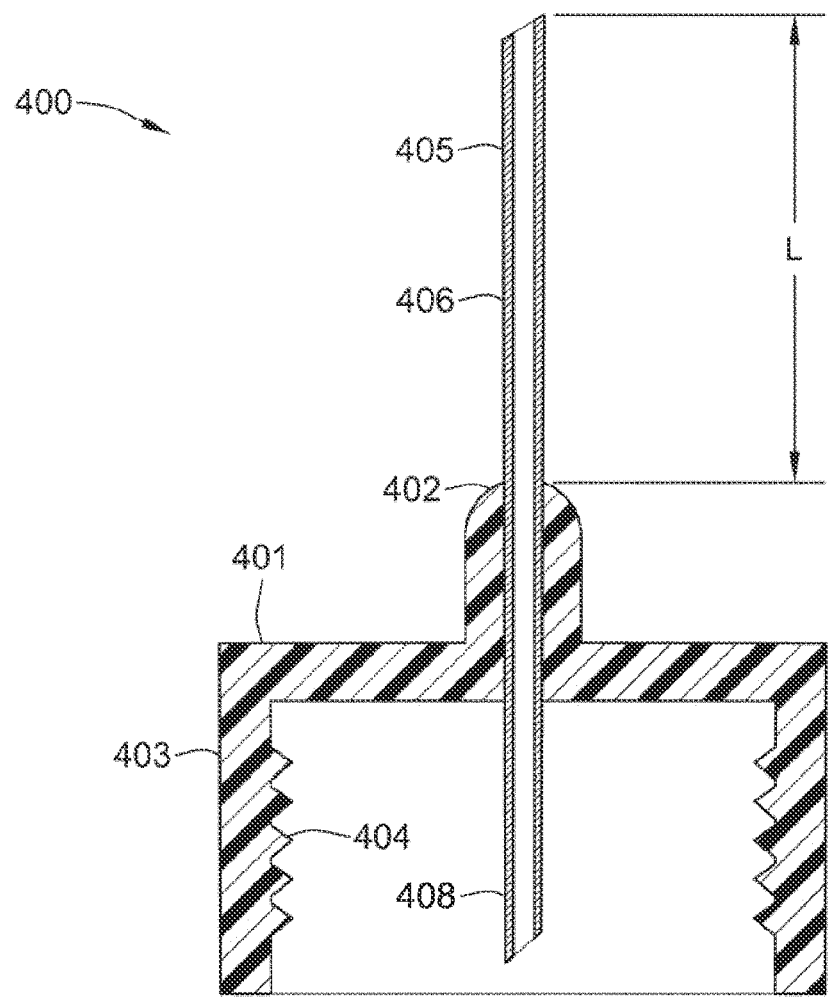
FIG. 6 illustrates one arrangement of a needle assembly that may be mounted on a distal end of the delivery device.
Figure 7:
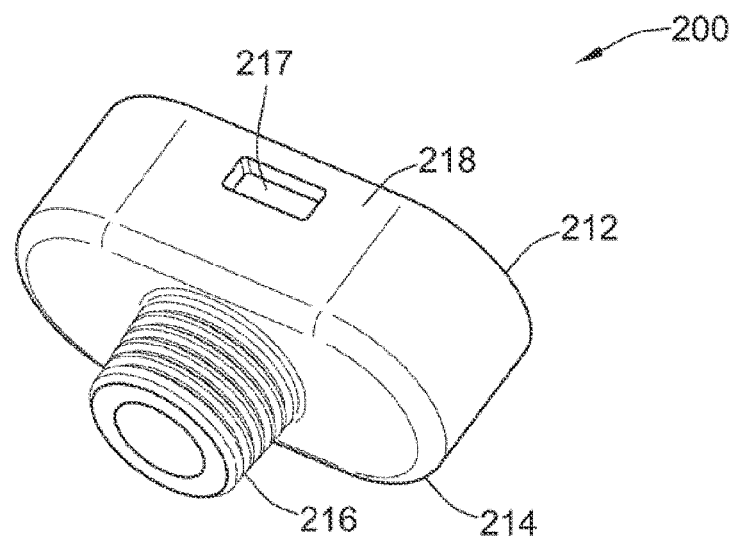
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
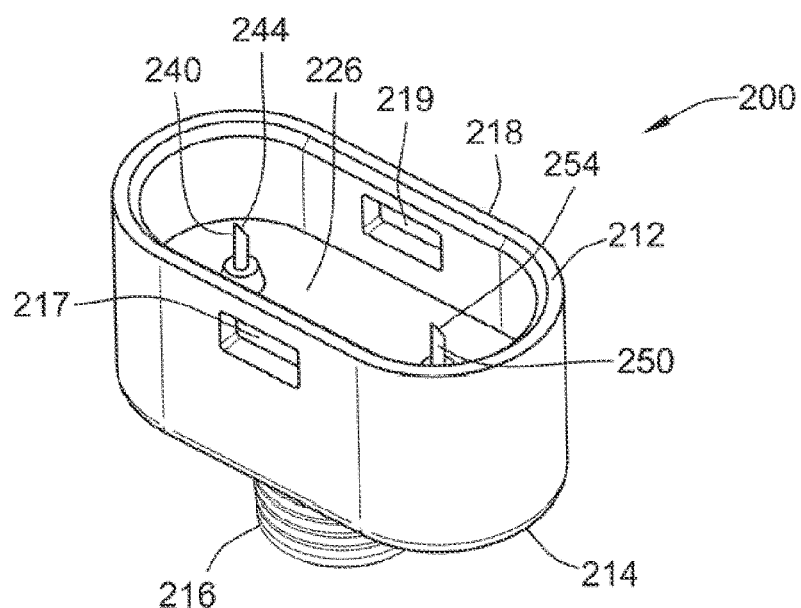
FIG. 8 illustrates another perspective view of the dispense interface illustrated in FIG. 4.
Figure 9:
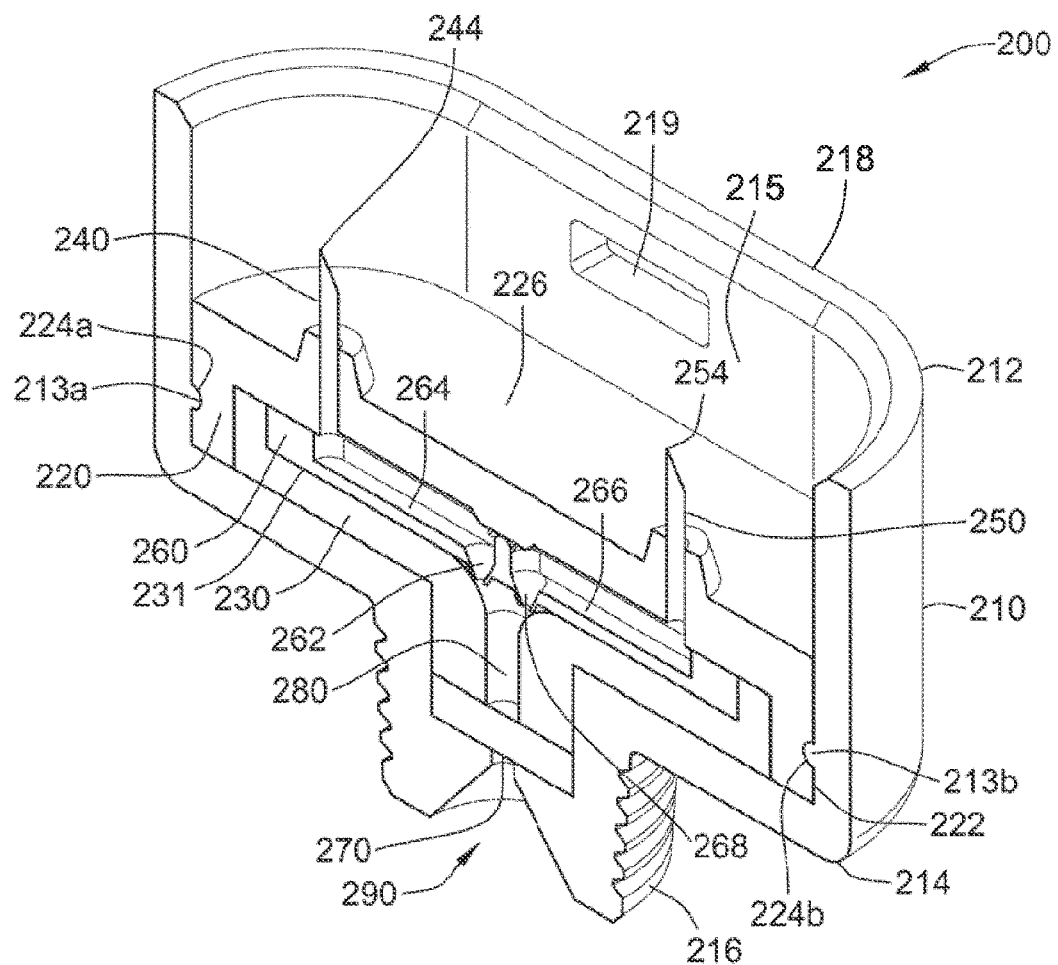
FIG. 9 illustrates a cross-sectional view of the dispense interface illustrated in FIG. 4.
Figure 10:
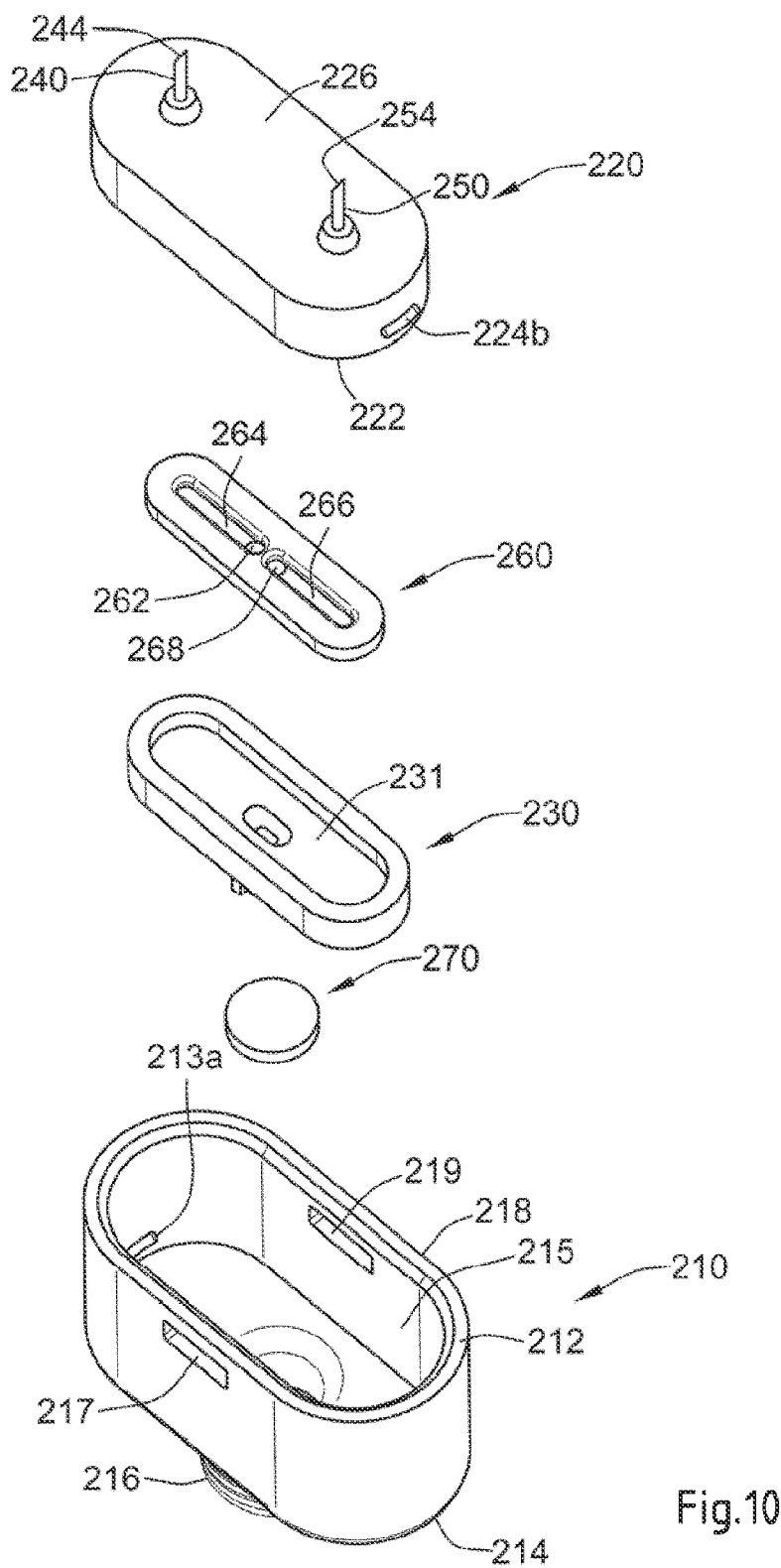
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
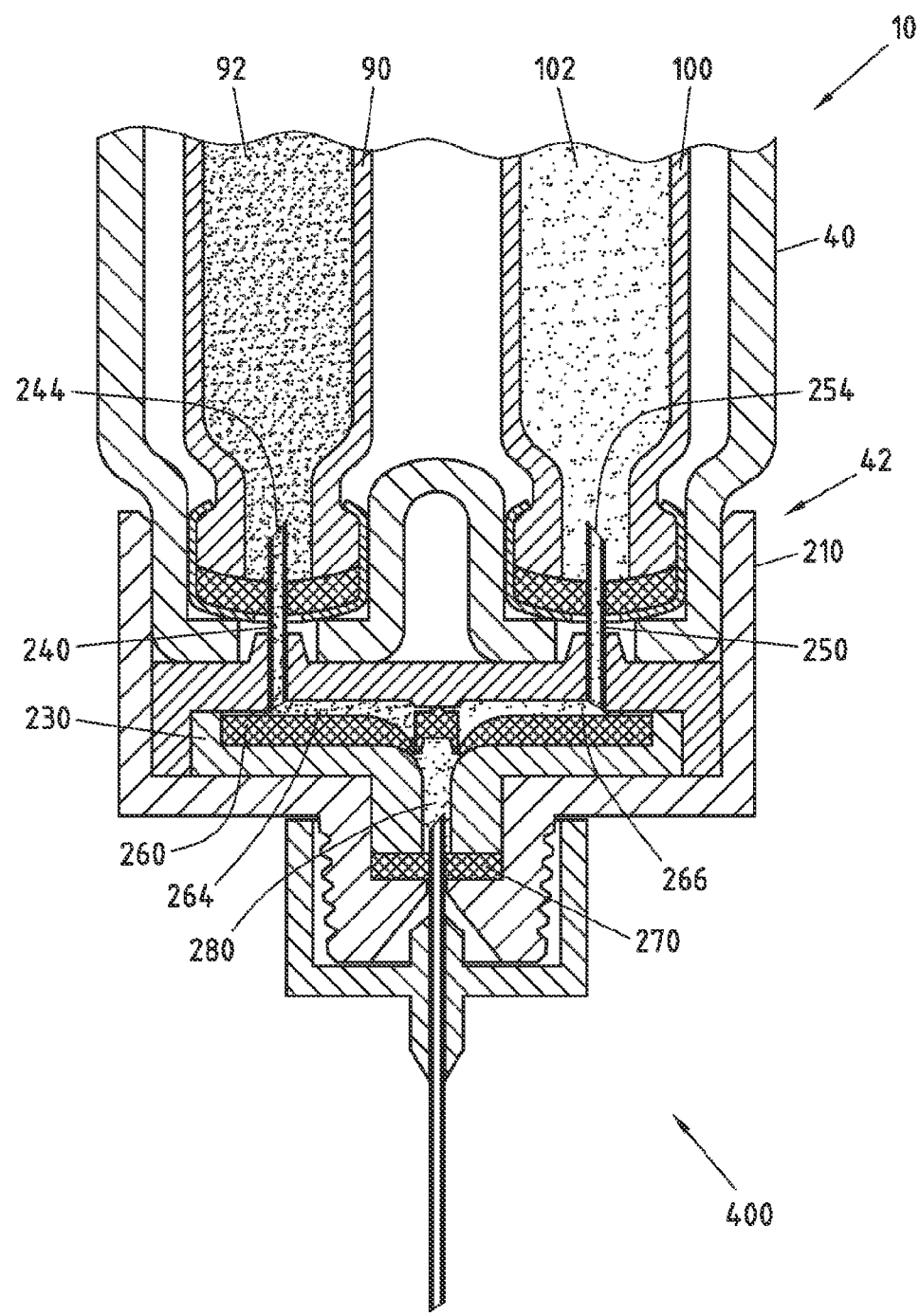
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100.

A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
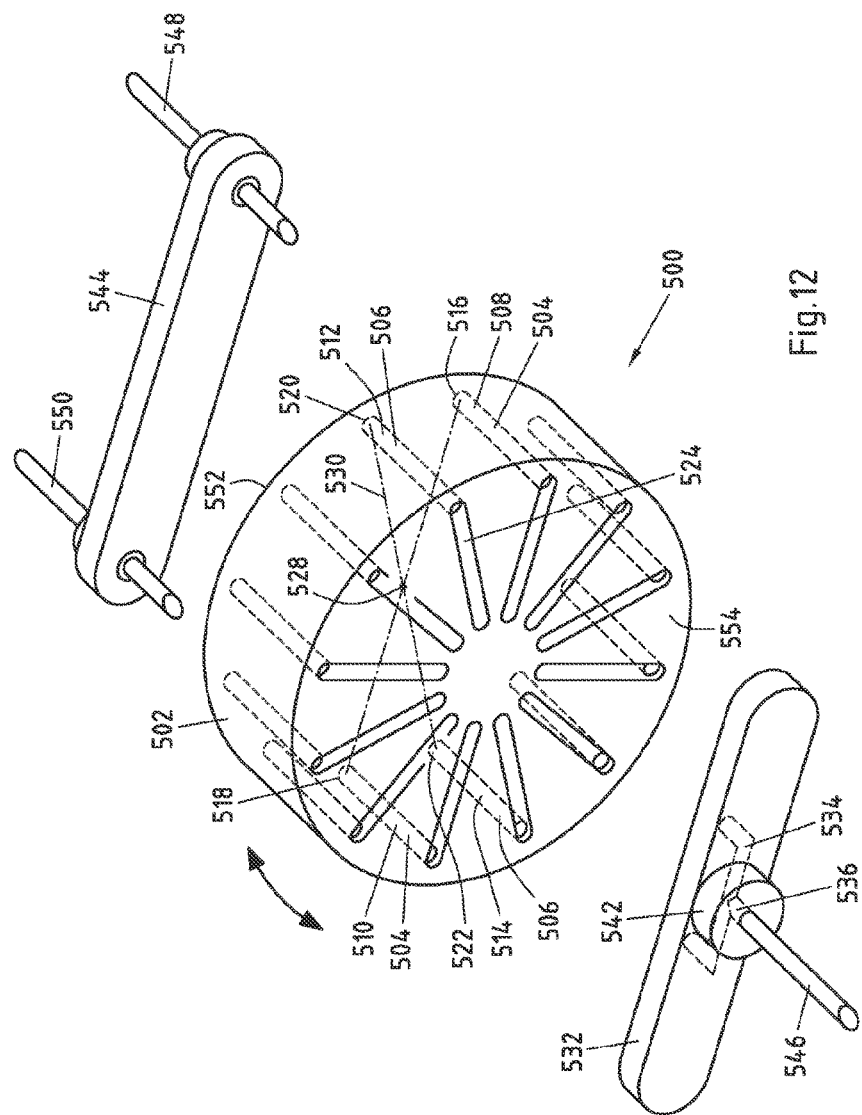
FIG. 12 illustrates an exploded view of a dispense interface according to the invention.

FIG. 12 illustrates an exploded view of a dispense interface 500 according to the invention. In the present example, the dispense interface 500 comprises a body 502. The body 502 is of a cylindrical shape. In particular, the body 502 is a drum 502. For instance, the body 502 can be formed by molding, in particular by injection molding.

The body 502 comprises multiple channel structures wherein in the present example only a first channel structure 504 and a second channel structure 506 are provided with reference signs for sake of clarity. The first channel structure 504 comprises a first inlet channel 508 and a second inlet channel 510. Each of the inlet channels 508, 510 comprises an inlet opening 516, 518. The inlet openings 516, 518 are arranged at an edge region of the body 502. Thereby, the inlet openings 516, 518 of the first channel structure 504 may be arranged on a straight line 530 which passes the center 528 of the proximal end surface 552 of the body 502.

An inlet channel 508, 510 may comprise a first channel part which is substantially linear and runs parallel with the axis of the body 502 and a second part following the first part, wherein the second part is substantially linear and runs parallel to the distal end surface of the body 502. The second part of the inlet channel is an open recess 524. A channel can be established by connecting a separate member 532 at the distal end 554 of the drum 502, as will be explained hereinafter.

The second channel structure 506 comprises a first inlet channel 512 comprising a first inlet opening 520 and a second inlet channel 514 comprising a second inlet opening 522. Preferably, all channel structures 504, 506 in the body 502 are similarly formed.

Furthermore, a connecting channel 534 and an outlet opening 536 are provided. In the present example, the connecting channel 534 and the outlet opening 536 are provided by a separate component 532 which can be tightly connected to the body 502. Thereby, the connecting channel 534 is configured for a fluid communication between the two inlet channels 508, 510, 512, 514 of (only) one channel structure 504, 506. In particular, only one channel structure 504, 506 can be in fluid communication with the outlet opening 536 at the same time.

Furthermore, a first double-ended needle assembly 544 comprising a first double ended needle 548 and a second double ended needle 550 is provided. The first double-ended needle assembly 544 can be tightly connected with the body 502, in particular, with a first inlet opening 516, 520 and a second inlet opening 518, 522 of one channel structure 504, 506. In particular, only one channel structure 504, 506 can be in fluid communication with the first double ended needle 548 and the second double ended needle 550 at the same time.

A second needle assembly 542 comprising an ejection needle 546 is provided. The second needle assembly 542 can be an integral part of the separate component 532 or a further separate part which can be tightly connected to the outlet opening 536 of the separate component 532.

Figure 13:
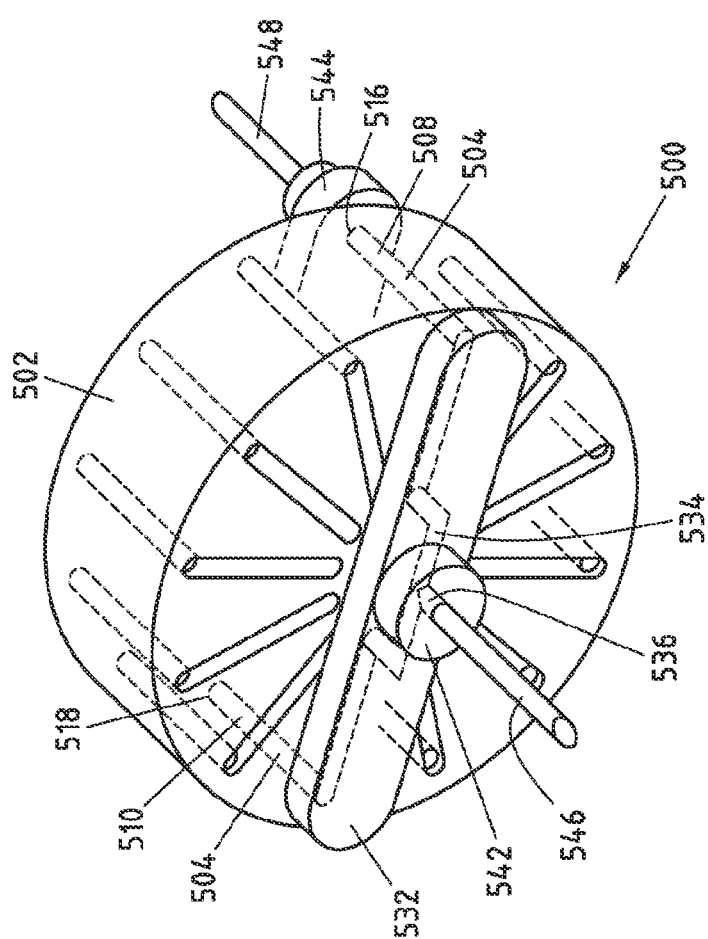
FIG. 13 illustrates a perspective view of the dispense interface illustrated in FIG. 12.

FIG. 13 illustrates a perspective view of the dispense interface 500 illustrated in FIG. 12. In FIG. 13, the first double ended needle assembly 544 is tightly connected to the body 502. In particular, the first double ended needle assembly 544 is tightly connected to the first channel structure 504. Furthermore, the separate component 532 is also tightly connected with the body 502. In particular, the separate component 532 is tightly connected to the first channel structure 504.

The illustrated dispense interface 500 can be attached to an ejection device, for instance manually by a user. After operating the ejection device, for instance, after ejecting at least one fluid from at least one reservoir of the ejection device, the dispense interface 500 can be removed from the ejection device. In addition, the separate component 532 and the first needle assembly 544 can be removed from the body 502. If the separate component 532 and the first double ended 544 needle assembly are single-use items, the respective components 532, 544 can be discarded.

If a further ejection should be performed, preferably a new separate component 532 and a new first double ended needle assembly 544 can be tightly attached to the body 502. In particular, the separate component 532 and the first double ended needle assembly 544 can be attached to an unused channel structure, like the second channel structure 506. Preferably, each channel structure of the body 502 is used for only ejection procedure. In the present example, since six channel structures are provided, the body 502 or drum 502 can be used six times. It shall be understood that according to other variants of the invention, there may be provided more or less channel structures.

Figure 14:
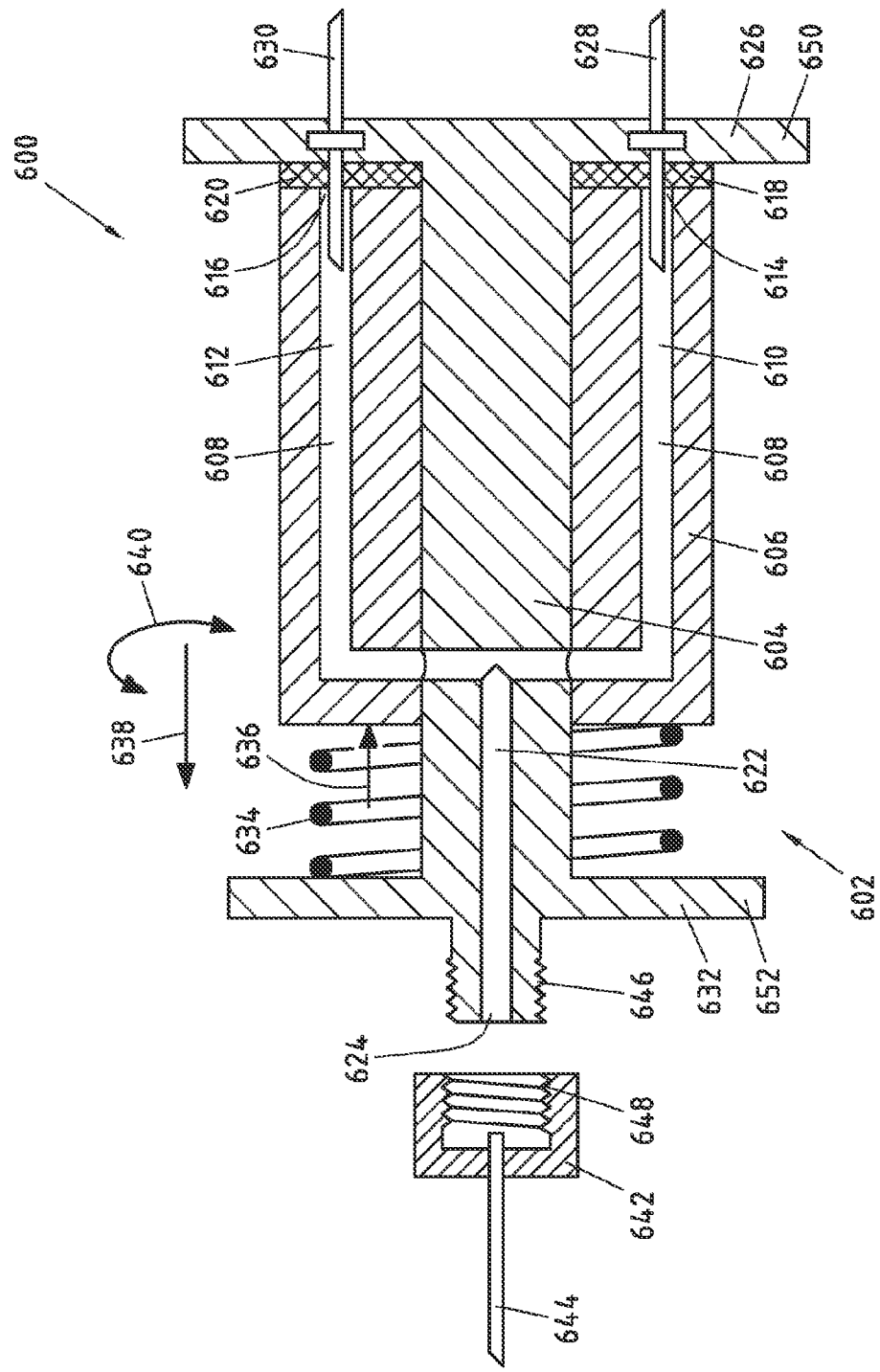
FIG. 14 illustrates a cross-sectional view of a further dispense interface according to the invention.

FIG. 14 illustrates a cross-sectional view of a further embodiment of a dispense interface 600 according to the invention. The dispense interface 600 comprises a body 602 having a first part 604 and a second part 606. The first part 604 has at least partly a cylindrical shape. The second part 606 is rotatably mounted to the first part 604.

Furthermore, the first part 604 comprises a first double-ended needle assembly 626 with a first double ended needle 628 and a second double ended needle 630. The first double-ended needle assembly 626 is an integral part of the first part 604. It forms the proximal end 650 of the first part 604.

At the distal end 652 of the first part 604, a stop element 632 is arranged. As can be seen from FIG. 13, an elastic element 634, in particular, a spring 634 is provided between the stop element 632 and the second part 606. The elastic element is configured to exert a force onto the second part 606 in the proximal direction 636. This causes that the second part 606 is pushed against the first double-ended needle assembly 626.

The second part 606 may be a rotationally symmetric part having a plurality of channel structures. In the present FIG. 14, a first channel structure 608 comprising a first inlet channel 610 and a second inlet channel 612 is illustrated. The further (not shown) channel structures may comprise the same shape as the first channel structure 608. Each inlet channel 610 612 comprises an inlet opening 614, 616. The first and the second inlet openings 614, 616 are sealed with a pierceable layer 618, 620. Preferably, all inlet openings are sealed by a pierceable layer. For instance, a rubber seal or film is provided. For instance, the layer 618, 620 may be made of metal, polymer and/or biopolymer. The layer 618, 620 can be attached to the proximal end surface of the second part 606 by any suitable process, like bonding techniques or thermal bonding techniques, such as fusion, laser techniques.

As can be further seen, the first part 604 comprises a connecting channel 622. The connecting channel 622 is configured for a fluid communication between the two inlet channels 610, 612 and an outlet opening 624 of the first part 604.

Furthermore, s second needle assembly 642 comprising a needle 644 is provided. In the present example, the second needle assembly 642 comprises a connecting element 648 which corresponds to a connecting element 646 of the first part 604. The first part 604 comprises an external thread 646 for providing a positive fit with the needle assembly 642 to provide a threaded engagement.

The illustrated dispense interface 600 can be attached, for instance manually by a user, to an ejection device for an ejecting process. Preferably, each channel structure is used for only ejection procedure. For attaching a new channel structure to the first double-ended needle assembly 626, the second part 606 can be pushed forward, preferably by a user, in a distal direction 638. Thereby, a force must be exerted which is larger than the force exerted by the elastic element 634. In case a spring 634 is employed, the force to be exerted depends at least on the spring constant.

When the second part 606 is pushed forward such that the double-ended needles 628, 630 are fully exposed, the second part 606 can be rotated. When a first and second opening of an unused channel structures is arranged opposite to the first and second double-ended needle 628, 630, a user can release the second part 606 and due to the force of the elastic element 634, the double-ended needles 628, 630 automatically puncture the sealing layer of the respective inlet openings. After a second needle assembly is attached to the dispense interface 600, the ejection device can be operated and at least one fluid of at least one reservoir can be ejected.

It shall be understood that a new channel structure can also be attached to the double-ended needle assembly 626 after the attachment to the ejecting device.

FIG. 15 shows embodiments of a valve arrangement in particular for a previously described dispense interface 500, 600.

The valve arrangements may for instance be integrally formed with another part of the dispense interface. Alternatively, the valve arrangement may for instance be manufactured separately from the other parts of dispense interface.

For instance, the valve arrangement may be inserted (e.g. potted/over-molded) into the body portion. For instance, the valve arrangement may at least partially be inserted (e.g. potted/over-molded) when the body portion are injection molded. For instance, the valve arrangement may at least partially be inserted (e.g. mounted) in a separate step after the body portion have been injection molded.

Figure 15A:
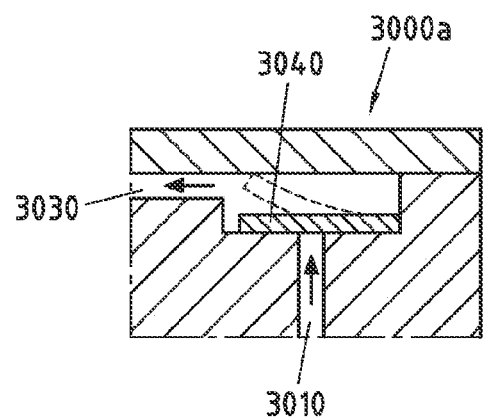
FIG. 15 illustrates valve elements, which can be used in a dispense interface according to the invention.

FIG. 15a illustrates a diaphragm/flap valve arrangement 3000a. The diaphragm/flap valve arrangement 3000a has an inlet 3010 and an outlet 3030. The inlet 3010 may for instance reside in fluid communication with one of the piercing needles 240, 250 of dispense interface 200 or with one of the piercing needles 548, 550 of dispense interface 500 or with one of the piercing needles 628, 630 of dispense interface 600, and the outlet 3030 may for instance reside in fluid communication with holding chamber 280 of dispense interface 200 or with the ejection needle 546 of dispense interface 500 or with the ejection needle 644 of dispense interface 600.

The diaphragm/flap valve arrangement 3000a has flexible diaphragm/flap 3040. When the fluidic pressure in the inlet 3010 is increased (e.g. during a dose priming or a dose injecting step), the diaphragm/flap 3040 will change from an un-stressed state to a stressed state. In the stressed state, the fluidic pressure bends the diaphragm/flap 3040 as indicated by the arrow in FIG. 15a so that the diaphragm/flap valve arrangement 3000a opens. In this stressed condition, the diaphragm/flap valve arrangement 3000a will allow fluid to flow from the inlet 3010 to the outlet 3030. When the fluidic pressure in the inlet is removed, the diaphragm/flap 3040 will return to its initial position and seal the inlet 3010, preventing backflow.

Figure 15B:
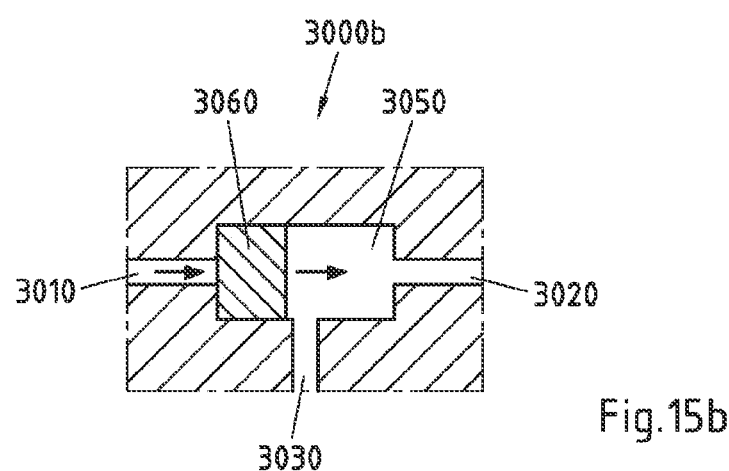

FIG. 15b illustrates a shuttling valve arrangement 3000b. The shuttling valve arrangement 3000b has a tube 3050. The tube 3050 has two inlets 3010, 3020 and an outlet 3030. In the tube 3050 a movable element 3060 (e.g. a piston or a ball) is arranged.

The diameter of the movable element 3060 corresponds to the diameter of the tube 3050 such that the movable element 3060 is movable between a first and a second (longitudinal) position in the tube 3050. In the first position (illustrated in FIG. 15b), the movable element 3060 seals the inlet 3010 and allows fluid flow from the inlet 3020 to the outlet 3030. In the second position (not illustrated), the movable element 3060 seals the inlet 3020 and allows fluid flow from the inlet 3010 to the outlet 3030. When the fluidic pressure in the inlet 3010 is for instance increased (e.g. during a dose priming or a dose injecting step), the movable element 3060 will be pushed towards the second position as indicated by the arrow in FIG. 15b.

Figure 15C:
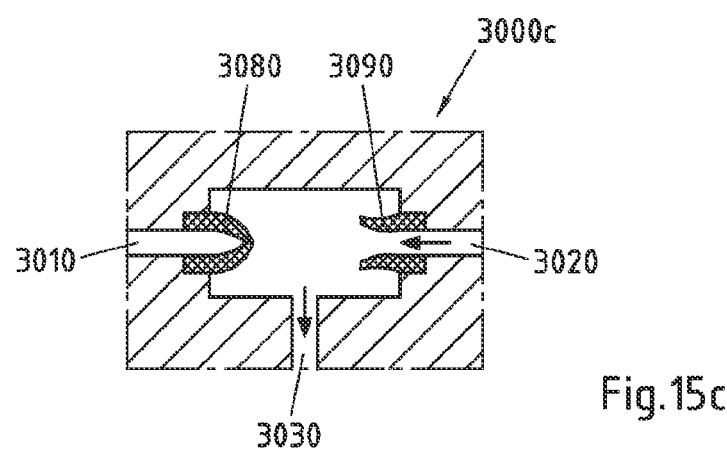

FIG. 15c illustrates a moulded duckbill valve arrangement 3000c. The moulded duckbill valve arrangement 3000c has a first and a second duckbill valve 3080, 3090. When the fluidic pressure in the inlet 3020 is increased (e.g. during a dose priming or a dose injecting step), the second duckbill valve 3090 will change from an un-stressed state to a stressed state. In the stressed state, the fluidic pressure inverts the naturally flattened shape of the duckbill valve as indicated in FIG. 15c so that the duckbill valve opens. In this stressed condition, the second duckbill valve 3090 will allow fluid to flow from the inlet 3020 to the outlet 3030. When the fluidic pressure in the inlet 3020 is removed, the second duckbill valve 3090 will return to its flattened shape and seal the inlet 3020, preventing backflow. The first duckbill valve 3080 operates in a similar manner as the second duckbill valve 3090 when the fluidic pressure is increased in the inlet 3010.

Figure 15D:
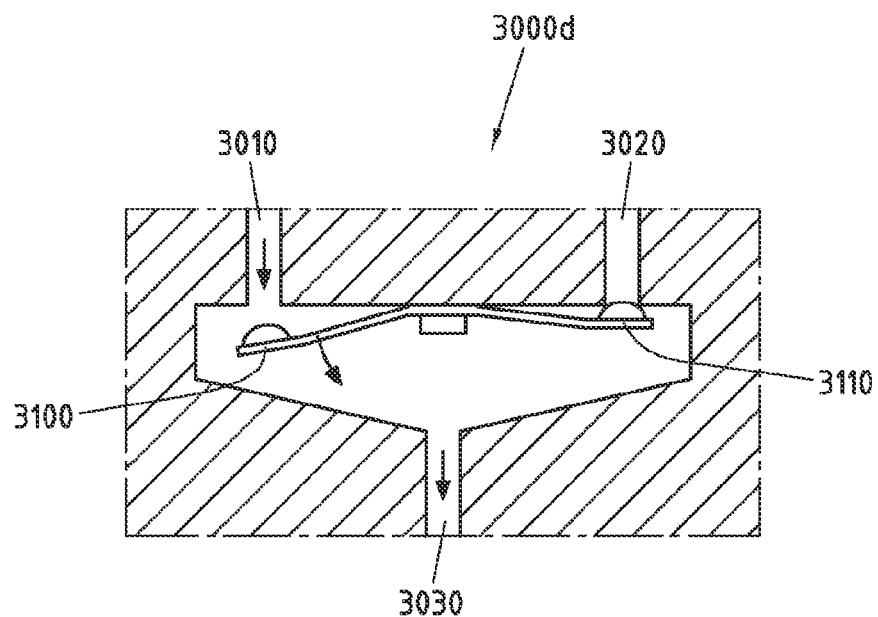

FIG. 15d illustrates a flat spring valve arrangement 3000d. The flat spring valve arrangement 3000d has a first and a second flat spring 3100, 3110. The first and the second flat spring 3100, 3110 may for instance be integrally formed.

When the fluidic pressure in the inlet 3010 is increased (e.g. during a dose priming or a dose injecting step), the first flat spring 3100 will change from an un-stressed state to a stressed state. In the stressed state, the fluidic pressure bends the first flat spring 3100 as indicated by the arrow in FIG. 15a so that the flat spring valve arrangement 3000d opens. In this stressed condition, the flat spring valve arrangement 3000d will allow fluid to flow from the inlet 3010 to the outlet 3030. When the fluidic pressure in the inlet is removed, the first flat spring 3100 will return to its initial position and seal the inlet 3010, preventing backflow. The second flat spring 3110 operates in a similar manner as the first flat spring 3100 when the fluidic pressure is increased in the inlet 3020.

Figure 15E:
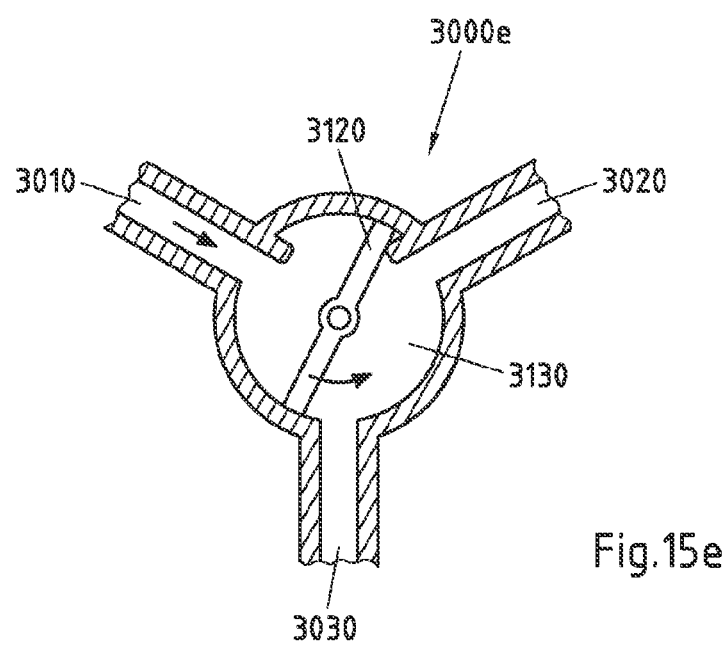

FIG. 15e illustrates a rotating flap valve arrangement 3000e. The rotating flap valve arrangement 3000e has a flap 3120 which is rotatably mounted in a valve chamber 3130. The valve chamber has two inlets 3010, 3020 and an outlet 3030.

The flap 3120 is rotatable between a first and a second position. In the first position (illustrated in FIG. 15e), the flap 3120 seals the inlet 3010 and allows fluid flow from the inlet 3020 to the outlet 3030. In the second position (not illustrated), the flap 3120 seals the inlet 3020 and allows fluid flow from the inlet 3010 to the outlet 3030.

When the fluidic pressure in the inlet 3010 is for instance increased (e.g. during a dose priming or a dose injecting step), the flap 3120 will be pushed towards the second position as indicated by the arrow in FIG. 15e.

Figure 16:
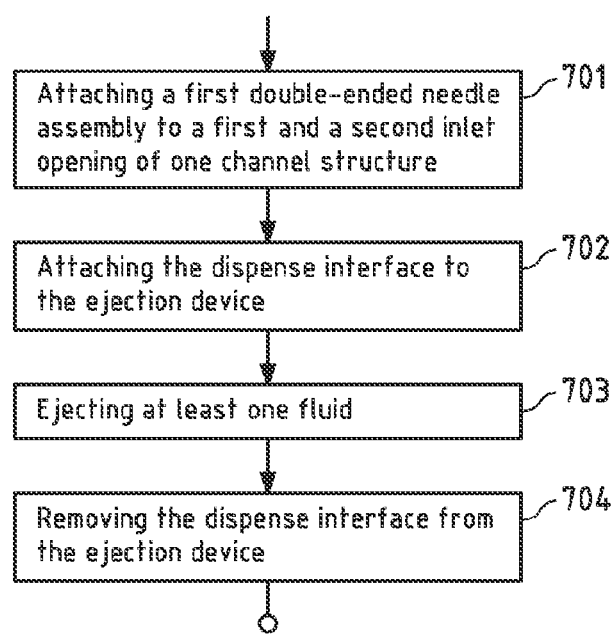
FIG. 16 illustrates a flowchart of a method for using a dispense interface according to the invention.

FIG. 16 illustrates a flowchart of a method for using a previously described dispense interface. In a first step 701, a first double ended needle assembly may be attached to the dispense interface. Preferable, the user attaches the first needle and the second needle to a first inlet opening and a second inlet opening, respectively, of an unused channel structure of the dispense interface. For selecting an unused channel structure, it may be required to rotate the body or a second part of the body of the dispense interface, as described hereinbefore. The user can recognise unused inlet openings e.g. by examining a provided seal layer.

It shall be understood that if a totally unused dispense interface is used, it may be necessary that in a previous step, a packaging must be removed by the user.

When the first double ended needle assembly is attached to the dispense interface, in an optional step, it may be necessary to attach a separate component to the body of the dispense interface. The separate component may already comprise a second needle assembly comprising an ejection needle. The separate component may be configured for establishing a fluid communication from the inlet channels of one channel structure via a connecting channel to an outlet opening of the dispense interface. In other variants of the invention, only the second needle assembly must be attached. For instance, a first part of the body, in particular, the outlet opening of the first part may comprise means for attaching a second needle assembly.

Then, in step 702, the dispense interface can be attached to the ejection device by the user. The needles of the first double-ended needle assembly provide the piercing needles for the first and the second reservoirs. This establishes a fluid tight connection between the primary fluid from the first reservoir with the outlet opening of the dispense device. Simultaneously, this establishes a fluid tight connection between the secondary fluid from the second reservoir with the outlet opening of the dispense device.

The user can then start an ejection procedure with the device in step 703.

After the ejection procedure, the user can remove the dispense interface from the ejection device (step 704).

If all channel structures have been used, the respective dispense interface can be discarded. Otherwise, the user can for instance put the dispense interface in a suitable storage box or the like. When a next ejection is required, the user can take the dispense interface from the storage box and can start the preparation of the dispense interface according to step 701. In particular, an unused channel structure can be attached by the user to a first double ended needle assembly.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly -Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, -continued H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface comprising:
a body comprising at least a first channel structure and a second channel structure,
wherein the first channel structure comprises at least a first inlet channel comprising a first inlet opening and a second inlet channel comprising a second inlet opening,
wherein the second channel structure comprises at least a third inlet channel comprising a third inlet opening and a fourth inlet channel comprising a fourth inlet opening,
wherein the first inlet opening of the first channel structure is configured for fluid communication with a first reservoir and the second inlet opening of the first channel structure is configured for fluid communication with a second reservoir,
wherein the third inlet opening of the second channel structure is configured for fluid communication with a third reservoir and the fourth inlet opening of the second channel structure is configured for fluid communication with a fourth reservoir, and
wherein at least one connecting channel configured for a fluid communication between at least one outlet opening and one of the at least two channel structures is provided in such a way that only one channel structure is in fluid communication with the outlet opening at the same time,
wherein at least one separate member comprising at least the at least one connecting channel and the at least one outlet opening is provided,
wherein the at least one separate member is configured for a fluid tight connection with the body.

2. The dispense interface according to claim 1, wherein a first double-ended needle assembly comprising at least a first double-ended needle and a second double-ended needle is provided,
wherein the first double-ended needle assembly is configured for a fluid tight connection with the at least two inlet openings of one channel structure.

3. The dispense interface according to claim 1, wherein the body is formed as a cylinder comprising a distal end surface and a proximal end surface,
wherein the at least two inlet openings of at least one channel structure are arranged at an edge region of the proximal end surface.

4. The dispense interface according to claim 3, wherein the at least two inlet openings of at least one channel structure are arranged on a straight line which passes the center of the proximal end surface.

5. The dispense interface according to claim 1, wherein the body comprises at least a first part and a second part,
wherein the first part is a cylindrical axis comprising the at least one outlet opening and the at least one connecting channel and
wherein the second part comprising at least the first channel structure and the second channel structure is at least rotatably mounted on the first part.

6. The dispense interface according to claim 5, wherein the first part comprises a first double-ended needle assembly,
wherein the first double-ended needle assembly is arranged at the proximal end of the first part in such a way that the first double-ended needle assembly is tightly connectable with the at least two inlet openings of one channel structure of the second part.

7. The dispense interface according to claim 5, wherein a stop element is arranged at the distal end of the first part,
wherein at least one elastic element is arranged between the stop element and the second part and
wherein the elastic element is configured to exert a force onto the second part into a proximal direction.

8. The dispense interface according to claim 7, wherein the second part is configured for releasing the fluid tight connection between the first double-ended needle assembly and the at least two inlet openings of a first channel structure by a movement in a distal direction and
wherein the second part is configured for establishing a fluid tight connection between the first double-ended needle assembly and the at least two inlet openings of a second channel structure by a rotational movement and a movement in a proximal direction of the second part.

9. The dispense interface according to claim 1, wherein at least one inlet opening is sealed by a pierceable material.

10. The dispense interface according to claim 1, wherein at least one part of the body is produced by injection molding.

11. The dispense interface according to claim 1, wherein at least one non-return valve is provided.

12. A system comprising:
a dispense interface according to claim 1, and
an ejection device,
wherein the dispense interface is attachable to the ejection device.

13. A method for using a dispense interface according to claim 1 comprising the steps of:
attaching a first double ended needle assembly to the inlet openings of one channel structure of the dispense interface and
attaching the dispense interface to an ejection device having at least two reservoirs such that a fluid tight connection is established between the at least two reservoirs and one channel structure of the dispense interface.

14. The method according to claim 13, further comprising the steps of:
ejecting a fluid from at least one of the reservoirs through the dispense interface and
removing the dispense interface from the ejection device.

* * * * *